(12) United States Patent
Bruns

(10) Patent No.: US 11,857,772 B2
(45) Date of Patent: Jan. 2, 2024

(54) NEEDLE SHIELD REMOVER

(71) Applicant: Owen Mumford Limited, Woodstock (GB)

(72) Inventor: Robert William Bruns, Woodstock (GB)

(73) Assignee: Owen Mumford Limited, Oxfordshire (GB)

( * ) Notice: Subject to any disclaimer, the term of this patent is extended or adjusted under 35 U.S.C. 154(b) by 338 days.

(21) Appl. No.: 17/032,867

(22) Filed: Sep. 25, 2020

(65) Prior Publication Data
US 2021/0093798 A1 Apr. 1, 2021

(30) Foreign Application Priority Data

Sep. 26, 2019 (GB) ...................................... 1913899

(51) Int. Cl.
*A61M 5/32* (2006.01)
(52) U.S. Cl.
CPC ......... *A61M 5/3204* (2013.01); *A61M 5/3213* (2013.01); *A61M 2005/3215* (2013.01)
(58) Field of Classification Search
CPC .............. A61M 5/3204; A61M 5/3137; A61M 5/3134; A61M 5/3102; A61M 5/3511; A61M 2005/3215; A61M 2005/3139; A61M 5/3104; A61M 5/31511
See application file for complete search history.

(56) References Cited

U.S. PATENT DOCUMENTS 8,579,866 B2 * 11/2013 Morgan .............. A61M 5/3137
604/187

* cited by examiner

*Primary Examiner* — Jason E Flick
*Assistant Examiner* — Justin L Zamory
(74) *Attorney, Agent, or Firm* — Quarles & Brady LLP

(57) ABSTRACT

A needle shield remover for removing a needle shield from a syringe. The needle shield remover comprises a receiving means to receive at least part of the needle shield, removing means to detach the needle shield from the syringe whilst it is present in the receiving means; and retaining means to temporarily retain the needle shield in the receiving means after removal of the syringe. Temporarily retaining the needle shield in the needle shield remover allows the needle shield remover to be reused. Additionally, by retaining the needle shield the needle shield remover prevents the needle shield from being lost or dropped on the floor when it is not retained within the needle shield.

17 Claims, 8 Drawing Sheets

NEEDLE SHIELD REMOVER

TECHNICAL FIELD

The present disclosure generally relates to a device for removing a needle shield. In particular, it relates to a reusable needle shield remover for removing a needle shield from the needle of a medicament delivery device.

BACKGROUND

Needle shields are used routinely to protect and maintain the sterility of a needle of a syringe prior to use by self-administering patients or by medical personnel. The shields are typically formed of a rubber enclosure, with either a flexible or rigid exterior cover surface, having a generally circular lateral cross-section surrounding a portion of the syringe needle cannula.

The manual removal of a needle shield from a syringe can cause accidental injury to the user, arising from abrupt release of the needle shield from the syringe followed by an unintended recoil of the user's hand back towards the uncovered needle, resulting in a "needle stick" injury.

To ameliorate this risk, some syringes now incorporate safety caps. These safety caps are configured to remove, and permanently capture, the needle shield upon removal of the cap from the syringe. A problem with such caps is that they typically require particular design needs to complement the medicament delivery device, and which leads to a second problem in that such single-use caps are an additional component to manufacture per-device, with associated material and waste costs.

It is therefore desirable to provide an improved device for removal of needle shields.

SUMMARY

Aspects and embodiments of the invention provide a needle shield remover configured to be releasably attached to a syringe, as claimed in the appended claims.

According to the present invention there is provided a needle shield remover for removing a needle shield from a syringe. The needle shield remover comprises a receiving means to receive at least part of the needle shield, removing means to detach the needle shield from the syringe whilst it is present in the receiving means; and retaining means to temporarily retain the needle shield in the receiving means after removal of the syringe. Temporarily retaining the needle shield in the needle shield remover allows the needle shield remover to be reused. Additionally, by retaining the needle shield the needle shield remover prevents the needle shield from being lost or dropped on the floor when it is not retained within the needle shield.

The needle shield remover may be provided with a passageway defined by a wall.

An opening in the rear of the passageway or the side of the passageway is configured to allow the at least part of the needle shield to be received in the needle shield remover.

The removing means may be an inward projection located on the passageway such that when the needle shield is inserted into the receiving means the inward projection engages the rear of the needle shield.

The removing means further include at least two rearwardly extending legs. Each of the rearwardly extending legs may be provided with an inward projection such that when the needle shield is inserted into the receiving means the inward projection engages the rear of the needle shield.

Placing the inward projection on the rearwardly extending legs facilitates insertion of a needle shield into the remover as, when the needle shield is inserted into the remover the legs flex outward, or away from the centreline of the passageway to allow the needle shield to be inserted. When the rear of the needle shield is reached, and before the syringe enters further into the remover the projections will site themselves at the end of the rear of the needle shield. This is because there is a depression (502) between the needle shield and syringe which is able to receive the projection. This facilitates correct positioning of the needle shield within the needle shield remover.

The retaining means may be positioned within the passageway. The retaining means may be a friction fit area within the receiving means, such as an area of elastomer, or one or more projections located at, or near to, the front opening of the passageway. The projections provide sufficient force to prevent the needle shield from moving in a distal direction within the needle shield remover when the syringe is removed from the needle shield.

Optionally, the projection is situated on a resilient front leg formed within a recess or cavity located at, or near to, the front opening of the passageway. The resilient front leg may be integral with and extend forwardly from the wall of the passageway at the rearward edge of the recess.

Alternatively, the retaining means may comprises a barrier mechanism, the barrier mechanism including a barrier member defining a passageway, the barrier member being moveable between a protruding position where the passageway and the passageway of the barrier member are not aligned and a recessed position where the passageway and the passageway of the barrier member are aligned.

The barrier mechanism may comprise an arm, and a resilient biasing member at one end of the arm, the resilient biasing member being configured to contact a wall of the device and bias the arm to the protruding position.

The barrier member may be provided with one or more teeth and/or areas of increased friction. The teeth are preferably situated such that they engage with the needle shield when the barrier member is in the protruding position and do not engage with the needle shield when the barrier member is in the recessed position.

The receiving means comprises a passageway defined by a side wall, and the passageway includes a cut-out in at least a portion of the side wall such that a needle shield may be inserted into the passageway through the cut-out. At least a part of the side wall forming an edge of the cut-out forms a ramp thereby facilitating entry of the needle shield into the passageway.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present invention will become more fully understood from the detailed description given below and the accompanying drawings which are given by way of illustration only, and thus are not to limit the scope of the present invention.

DETAILED DESCRIPTION

Figure 1A:
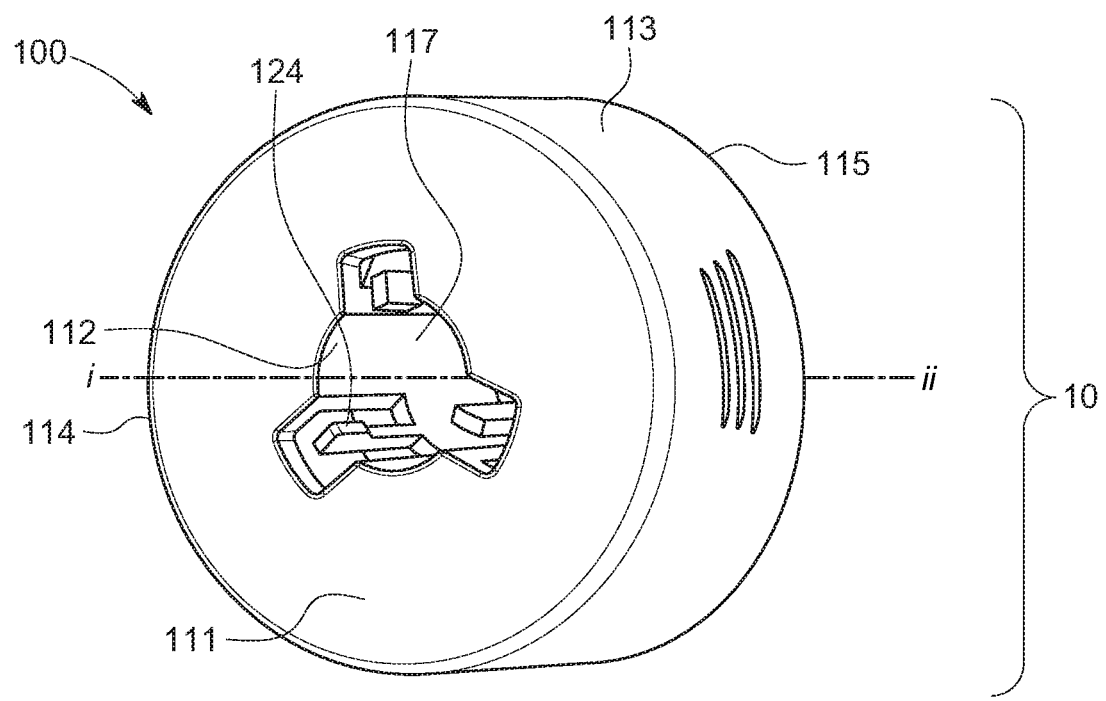
FIGS. 1a-1d show an embodiment of a needle shield remover according to the present invention.
Figure 1B:
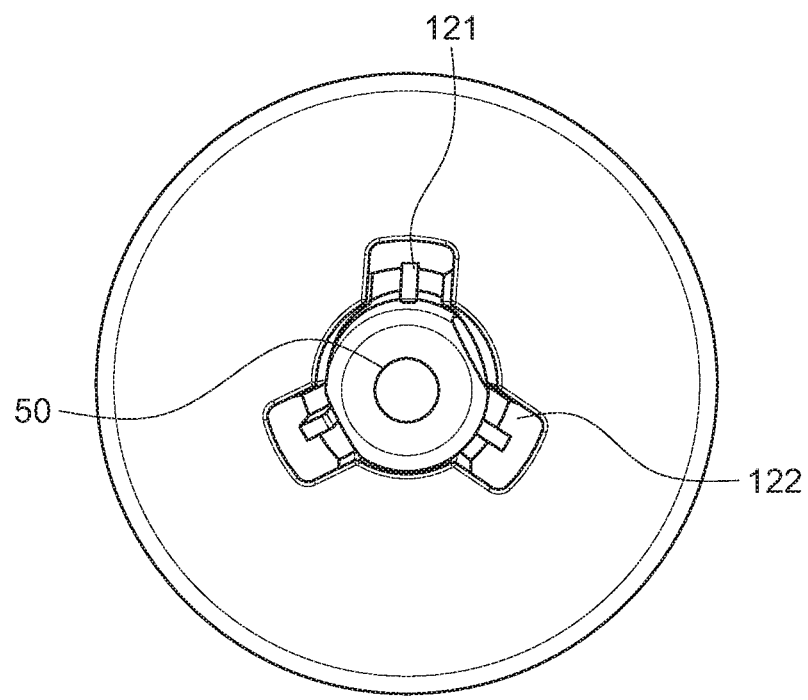

Certain terminology is used in the following description for convenience only and is not limiting. The word "distal" refers to the front, or patient, end of the device. The word "proximal" refers to the rear, or syringe user, end of the device. The term "longitudinal", with or without axis, refers to a direction on an axis through the device in the direction of the longest extension of the device. The term "radial" or "transverse/transversal", with or without axis, refers to a direction generally perpendicular to the longitudinal direction, e.g. "radially outward" would refer to a direction pointing away from the longitudinal axis.

The Figures illustrate a reusable needle shield remover (100, 200, 300, 400) provided to remove a needle shield (50) from a syringe (501).

FIGS. 1a-1d show an embodiment of a needle shield remover according to the invention. In this embodiment, the remover device (100) has a passageway (117) along a central longitudinal axis (i-ii). The passageway (117) has a cylindrical side wall (123) which extends proximally from a front opening (112) to a rear opening (118).

The passageway (117) has an internal diameter great enough so that a needle shield (50) can be received within the passageway (117). The passageway (117) is elongate and of sufficient length to at least partially enclose the needle shield (50). In use, the needle shield (50), is received in the passageway (117) by insertion of the needle shield (50) through the rear opening (118)

Located at the rear end of the passageway (117) are means to remove the needle shield (50) from a syringe. In this embodiment, the rear end of the passageway (117) terminates with two rear legs (119). The rear legs are configured to flex radially outwards as the needle shield is inserted into the device. Projections (120) on the internal surface of the rear legs (119) extend radially inwards from the circumference. The proximal face of each projection is angled away from the rear of the device to allow the needle shield (50) to easily pass over the projection (120) as the needle shield (50) is inserted into the needle shield remover (100). The distal face of each projection (120) is flat. The projections (120) are situated part way down the rear legs (110) of the needle shield remover (10).

In use, the needle shield (50) is inserted into the passageway (117) past the projections (120). As the syringe (not shown) is then removed from the needle shield (50), the distal face of each projection (120) comes into engagement with the proximal end of the needle shield (50), thereby preventing further rearward movement of the needle shield (50) with the syringe.

In a first embodiment, as shown in FIG. 1a-1d, located at the front end of the passageway (117) are one or more cut outs (122). In each of the cut outs (122), extending distally from the distal end of the side wall (123) of the passageway (117), is a resilient front leg (121). Each front leg (121) is provided with a projection (124) extending from the leg (121) towards the central axis of the passageway (117). Thus the diameter of the front opening of the passageway (117) including a front leg (121) is less than the diameter between two opposite parts of the wall (123) of the passageway (117).

Figure 1C:
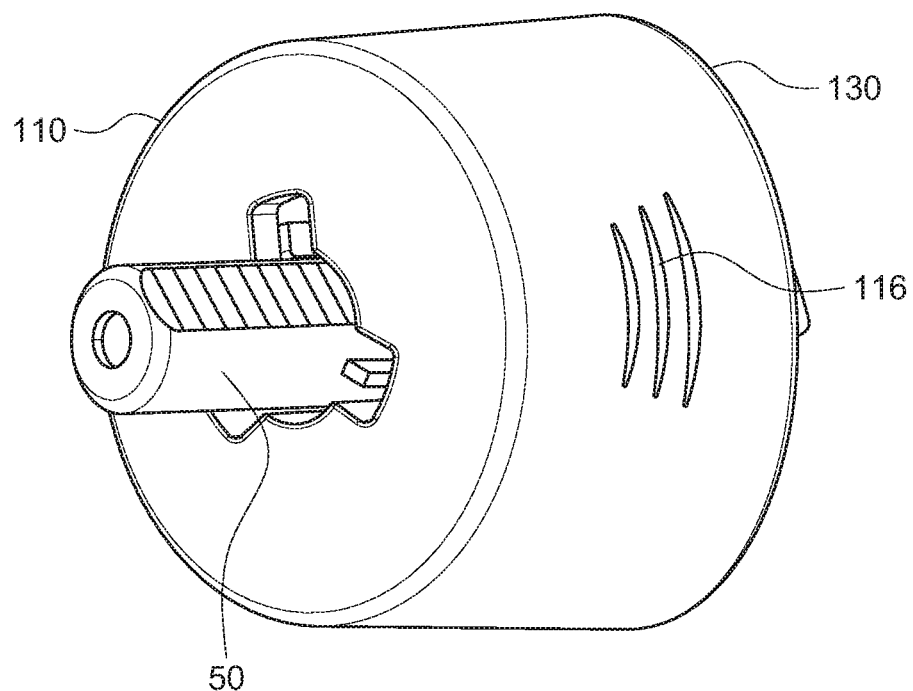
Figure 1D:
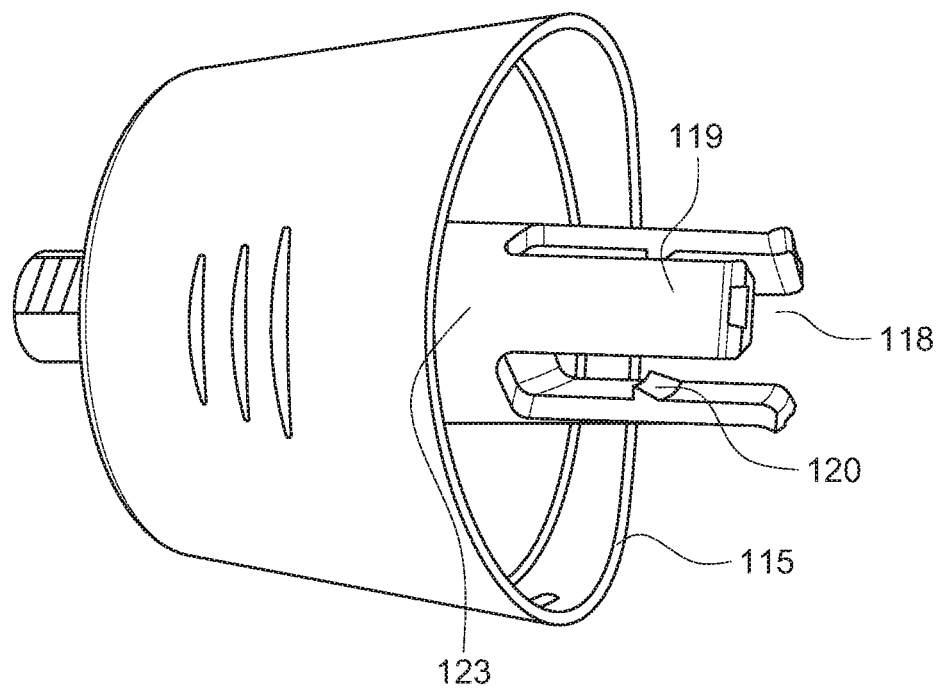

In use, the needle shield (50) is inserted into the passageway (117) until the forward end exits the front opening of the passageway (117) as shown in FIGS. 1c and 1d. The cut outs (122) allow each front leg (121) to flex radially outwards (122) as the needle shield (50) passes over the projection(s). As the needle shield (50) is removed from the syringe, the projections (124) on the resilient front legs (121) engage the outer surface of the needle shield (50) thereby restricting distal movement of the needle shield (50) further along the passageway. The needle shield (50) is now retained within the needle shield remover.

In order for the needle shield (50) to be removed from the passageway (117), the user grasps the protruding needle shield (50) at the front end and pulls the needle shield (50) further in a distal direction against the friction from the flexed resilient front legs (121) gripping the exterior surface of the shield (50). The removed needle shield (50) may disposed of, and the remover device (10) is now able to be reused.

The needle shield remover is further provided with a front face (111) and an outer side wall (113). While FIG. 1d illustrates an open-cup shape to the needle shield remover housing (10), whereby the inner cylindrical wall (123) defining the passageway (117) extends proximally from the front opening, an enclosed hollow or solid form to the housing could be envisioned, whereby the rear edge (115) is joined to the inner cylindrical wall. Optionally, the shape of the front face (111) may by fully or partially circular, elliptical, square, rectangular or any other shape. Preferably, the front face (111) may have a circular or elliptical shape radiating from the central longitudinal axis. Optionally, while a generally symmetrical shape about the longitudinal axis of the housing (10) is illustrated herein, alternative aesthetic shapes to, for example, facilitate an easier hand grip of the housing such as a grip handle, could be envisioned as within the scope of the invention.

The cylindrical side wall (113) of the housing (10) may be of uniform diameter along its length, or may be partially flared so as to form, for example, a truncated cone. Optionally, the side wall (113) may comprise indents or protrusions (116) to further facilitate manual gripping of the device by a user.

While the embodiments presented herein illustrate the device as centred uniformly about a longitudinal axis i-ii, it is conceivable that an overall aesthetic shape to the device may configure the position of the passageway (117) at any location on the front face (111) of the housing (10).

The needle shield remover may be made from any suitable material, or a combination thereof, for example plastic or metal. Preferably, the remover device is made from a rigid or flexible plastic. Optionally the projections (124) may be integral to, and made from, the same material as the front legs (121). Alternatively, the projections (124) may be an elastomeric material such as rubber.

The skilled person will understand that the above description is by way of example only.

For example, the remover device (10) may not be provided with a front face (111) and outer side wall (113) but rather may only be provided with an inner side wall (123). The inner side wall (123) may be provided in any suitable shape and thickness. Additionally, the inner side wall (123) may be provided with a means for gripping the needle shield remover (10). For example, the inner side wall (123) may be provided with an elastomeric sleeve extending at least part way along the wall (123) or with shaped indents and protrusions such as those shown and described with reference to the outer side wall (113) above. Additionally the needle shield remover (10) may be provided with an outer side wall (113) but not a front face (111) with the inner side wall (123) and outer side wall (113) meeting at a junction.

Although the projections (120) on the rear legs (110) of the needle shield remover (10) have been described as being part way down the rear legs (110) the skilled person will understand that the location may be varied. For example, the projections (120) may be located close to, or at the proximal ends of, the rear legs (110). Additionally, the device may not be provided with rear legs but may be provided with alternative means which allows passage of the needle shield (50) past the projections (120) when the needle shield (50) is inserted into the passageway (117). The skilled person will understand that the projections (120) may be of any suitable angle relative to the rear legs (110)

Alternative means for removing the needle shield could also be envisioned by the skilled person, such as for example an elastomeric or braided sleeve configured as a friction fit to surround and grasp the needle shield (50) but to allow for movement of the removed needle shield (50) forwards within the passageway (117).

Optionally, the front of the passageway (117) may not be provided with cut outs (122) as described previously and shown in FIGS. 1a-1d but instead may be provided with recesses where the diameter of the inner side wall (123) at the recesses is greater than the rest of the inner side wall (123). These recesses provide a cavity into which the front legs can be pushed when the needle shield (50) is inserted into the needle shield remover (10).

In a second embodiment, as shown in FIGS. 2a-2e, like features are denoted by the same reference number as for FIG. 1a-1d, and function in the same way, unless otherwise described. A front end of the housing (20) is set back from the front end (110) of the outer side wall (113), thereby defining an interior wall (201). A front cover (202) comprises a plurality of projections (221). The plurality of projections (221) are received by complementary recesses (207), present in the inner wall (201). The recesses (207) are positioned and configured to receive the projections (221) thereby holding the front cover (202) in engagement with the interior wall (201), thereby forming a cavity.

Within the cavity is provided a barrier mechanism (203-206). The mechanism comprises a manual actuator such as a button (203), an arm (204), and a resilient biasing member (206). The manual actuator (203) is situated within a recess (222) in the side wall (113). The manual actuator (203) is connected to the arm (204) which projects from the cavity through a gap in the side wall (113), between the interior wall (201) and the front cover (202). At the opposite end of the arm (204) to the button (203), there is provide a barrier member (205) comprising a circular outer wall (205) with inner passageway (224). The diameter of the outer wall (205) defines the inner passageway (224) to have the same diameter as the passageway (117). Finally, at the opposite end of the barrier member (205) to the arm (204), there is provided a biasing member (206). The biasing member (206) comprises a resilient arcuate wall (226) connected to the barrier member (205) by two arms (225). Each arm (225) is connected at one end to the barrier member (205) and at the other to the arcuate wall (226).

When the mechanism is sited within the cavity, as previously stated, the actuator (203) is situated within a recess in the side wall. The arm (204) passes through the gap (222) in the side wall (113). The barrier member (205) is positioned such that the passageway (224) of the barrier member (205) is offset from the passageway (117). The offset means that at least a portion of the barrier member (205) overlaps with the passageway (117), resulting in an effectively reduced diameter of the open passageway. The arcuate wall (226) of the biasing member is in contact with the inner surface of the housing side wall (113).

The moulded protrusions (207) on the interior wall (201) provide a path in which the arm (204) of the mechanism sits, allowing only a limited range of transverse radial movement of the arm (204) and therefore the mechanism.

Figure 2A:
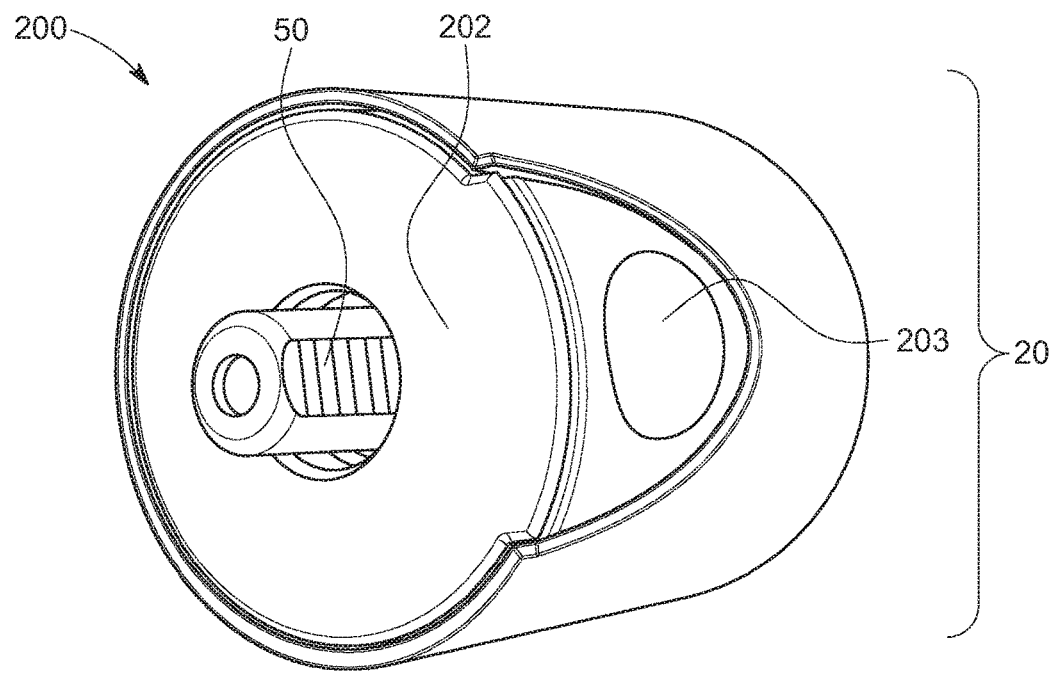
FIGS. 2a-2e show another embodiment of a needle shield remover according to the present invention.
Figure 2B:
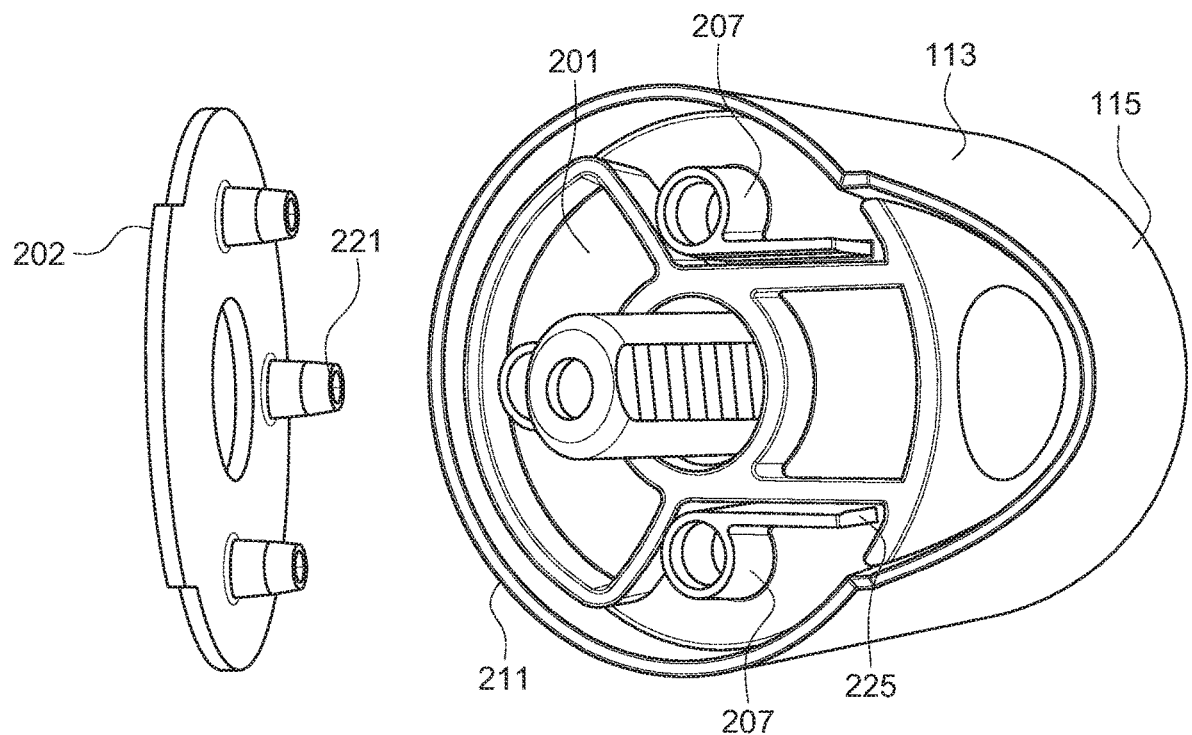
Figure 2C:
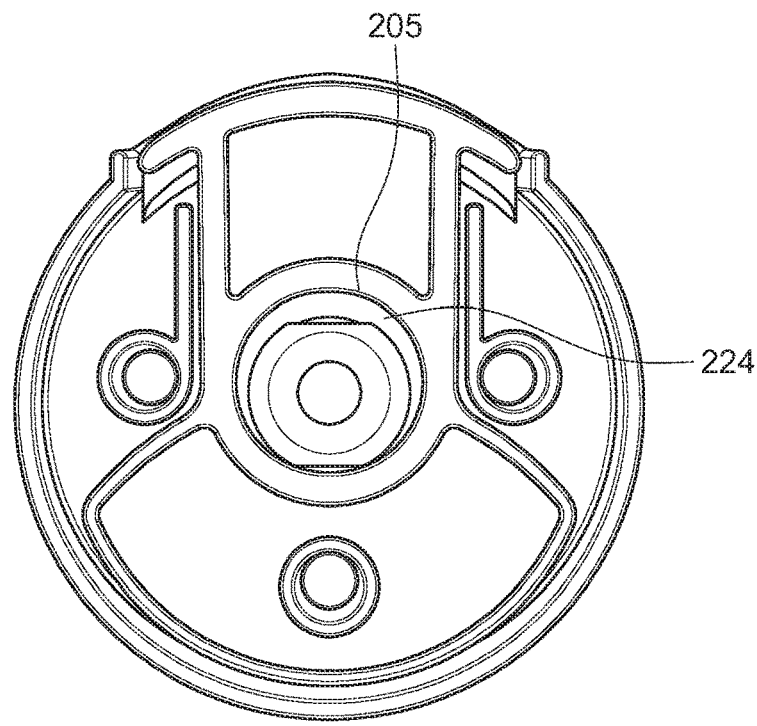

At a first position, the barrier member passageway (224) and the passageway (117) are offset, as shown in FIG. 2c. The offset is sufficient that when a needle shield (50) is inserted into the passageway (117) a sideways frictional force is applied by the barrier member (205) to the needle shield (50). The external surface of the needle shield (50) is gripped by the wall of the barrier member (204) sufficiently that when the needle shield (50) has the force exerted on it by the projections (120) during syringe removal further distal axial movement is prevented.

Figure 2D:
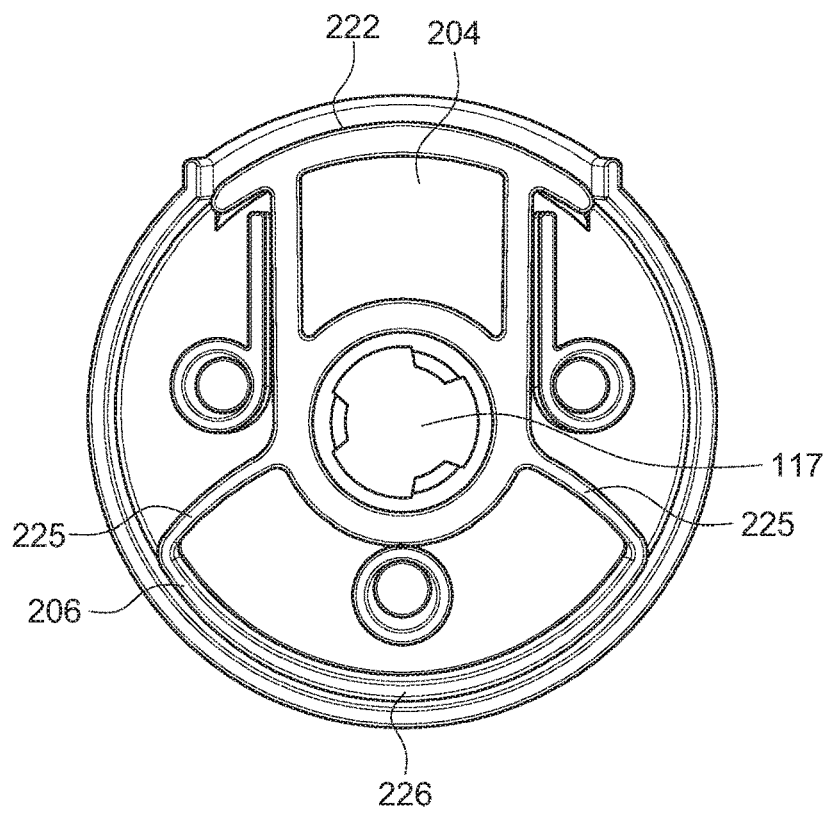
Figure 2E:
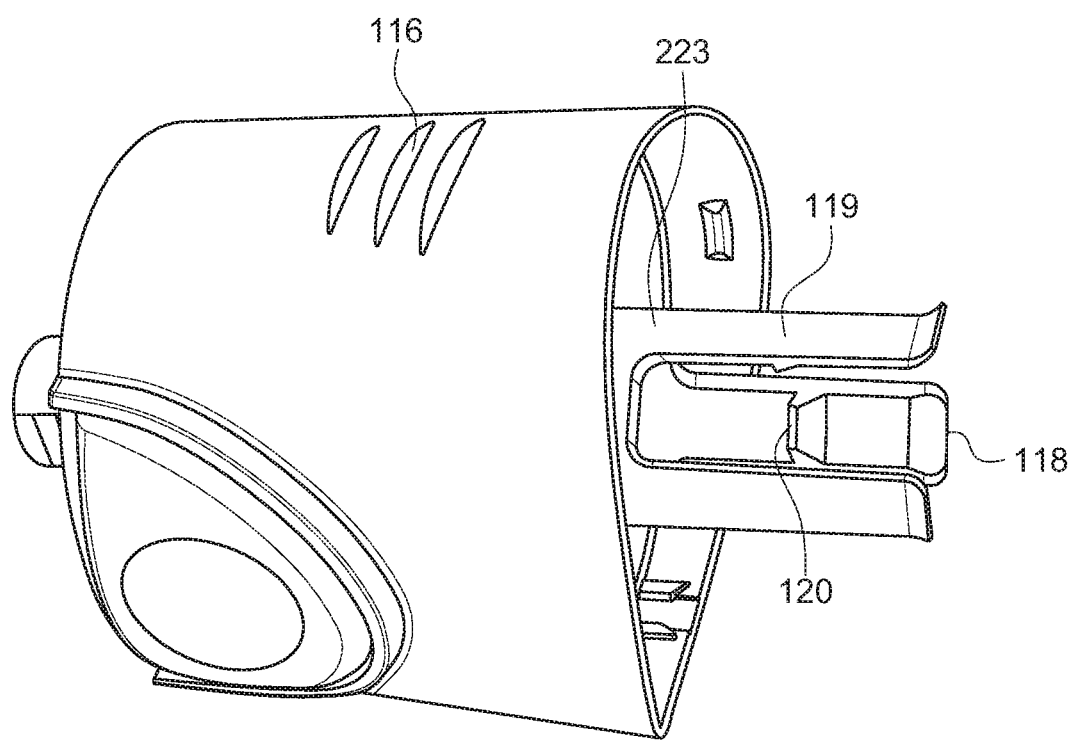

Applying pressure to the actuator (203) causes the arm (204) and thus the barrier member (205) to move radially inwards to a second position. In this second position the passageway of the barrier member is aligned with that of the passageway (117), as shown in FIG. 2d. This movement is against the bias of the arcuate wall (206). In this second position, exit of the retained needle shield (50) is enabled due to the lining up of the passageways (224, 117) and thus the removal or reduction of the frictional force exerted by the barrier member (205).

When pressure is removed from the actuator (203), the arcuate member (206) returns to its original shape. This causes the barrier member (205) to return to its first position, thereby causing the passageways (223, 117)) to once more be offset.

Optionally, at least a portion of the wall of the barrier member (204) may be provided with material to increase the friction between the needle shield (50) and the wall of the barrier member (204). This material may be an elastomer, for example, rubber. Alternatively, the barrier member (205) may be provided with teeth which engage with the surface of the needle shield (50) and are disengaged from the surface of the needle shield (50) when the actuator is depressed. The teeth may be made, for example, from a rigid plastic material or from metal. To remove the needle shield from the device in this configuration, the actuator is pressed to release the grip of the barrier member (204) on the needle shield (50).

In the instance where the frictional force exerted by the barrier member (205) on the needle shield (50) is sufficient to prevent proximal movement of the needle shield (50) during removal of the syringe the needle shield remover may not be provided with the rearwardly extending legs (119) and/or projections (120) as described previously with reference to FIGS. 1a-1d Alternatively, the effective diameter of the offset passageways of the barrier member (205) and the needle shield remover (200) prevents the exit of any portion of the needle shield (50), and as a result the needle shield is completely contained within the passageway. The needle shield (50) may be removed by depressing the button and allowing the needle shield to fall from the needle shield remover as no frictional force is required to prevent axial movement of the needle shield (50) out of the needle shield remover.

The recesses (207) may be recesses (204) formed by the inner wall, or recess walls projecting forward from the inner wall. As will be understood by the skilled person, although the recesses are described as being present on the inner wall, the recesses may be present on an inner surface of the front cover with complementary projections present on the inner wall. Additional combinations of projections and recesses may be present on the inner wall and the front cover. Additionally, the cavity may be provided at an intermediate position between the front end of the needle shield remover and the rear end of the needle shield remover. In this instance the cavity will be extended and the front wall adapted accordingly.

Figure 5:
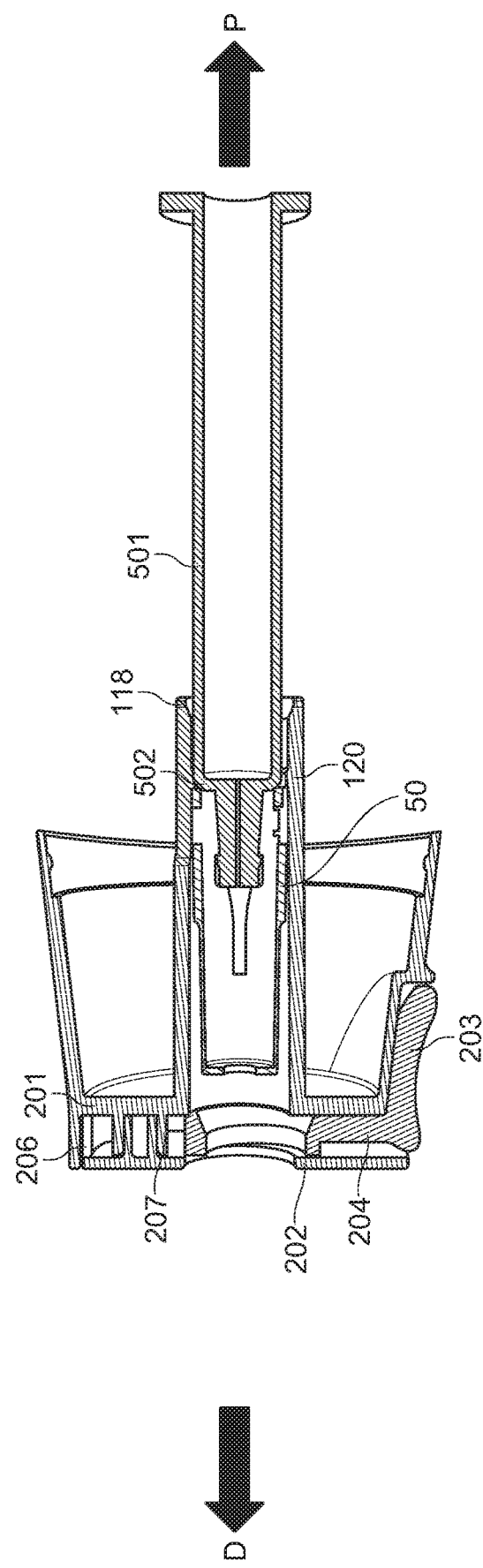
FIG. 5 shows the embodiment of FIGS. 2a-2e when connected to a needle shield of a syringe.

FIG. 5 illustrates the device of the second embodiment in use with a syringe (501) inserted into the passageway (117)

Figure 3:
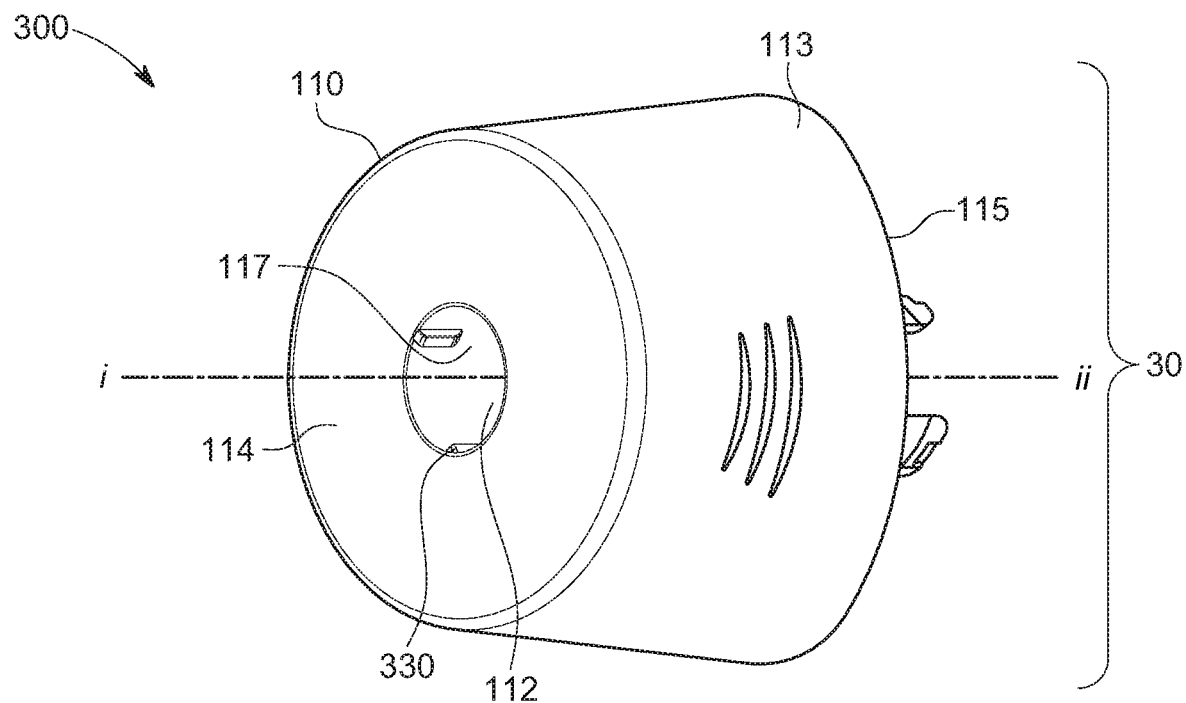
FIG. 3 shows another embodiment of a needle shield remover according to the present invention.

In a third embodiment, as shown in FIG. 3, like features are denoted by the same reference number as for FIG. 1, and function in the same way, unless otherwise described. In this embodiment, the passageway of the housing is provided with means to hold the needle shield in frictional engagement with the passageway. This prevents the needle shield from exiting the forward opening of the passageway upon removal of the syringe. The means to hold the needle shield is at least one projection (330) located at, or near to, the front opening (112) of the inner cylindrical wall defining the passageway (117). The at least one projection holds the needle shield with sufficient frictional engagement that any force created through the syringe removal does not result in the needle shield exiting the forward opening of the passageway.

Other means may be provided for holding the needle shield in the passageway through frictional engagement, for example the inner wall of the passageway may be provided with one or more sections of an elastomer such as rubber. The sections may be, for example, longitudinal strips, one or more strips formed on the surface of the inner cylindrical wall, or transversely extending strips.

Figure 4:
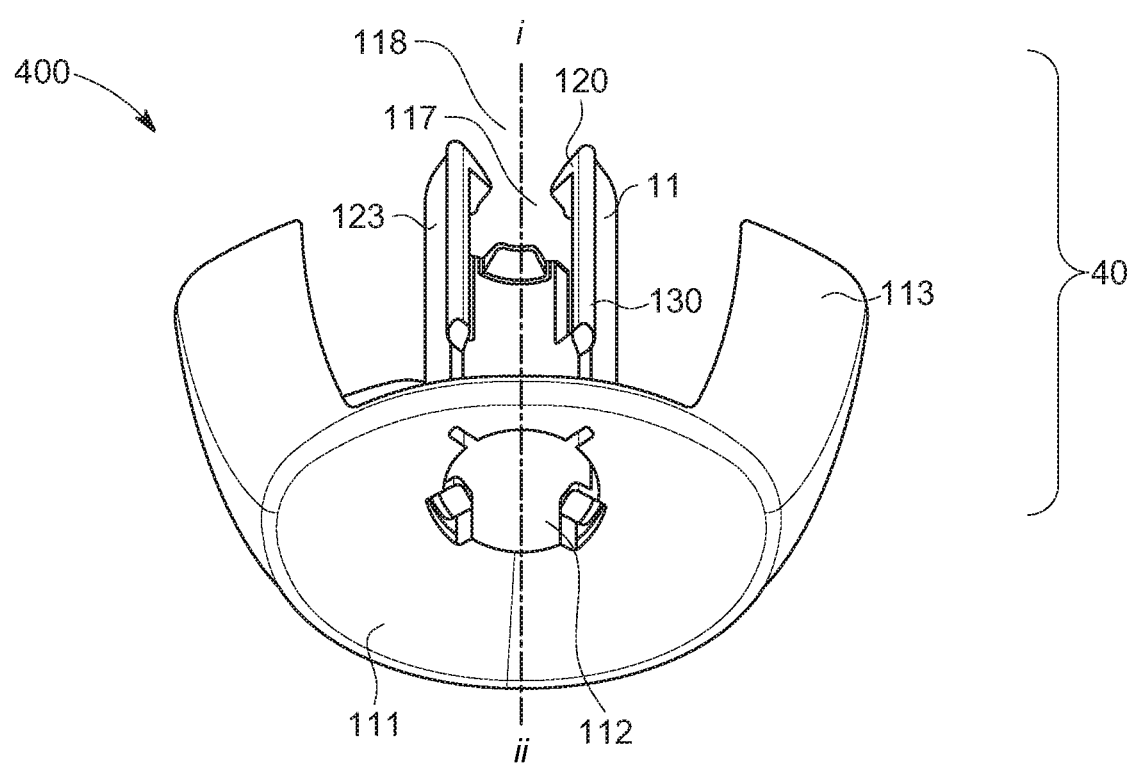
FIG. 4 shows another embodiment of a needle shield remover according to the present invention.

In a fourth embodiment, as shown in FIG. 4, a needle shield remover (400) is presented in which both the cylindrical sidewall (113) and passageway (117) define cut-out sections that allow insertion of the needle shield (50) into the passageway (117) from the side of the needle shield remover (100). The cut out is such that the width of the cut out is less than the diameter of a needle shield (50). The inner sidewall (123) of the passageway (117) is formed from a material that flexes sufficiently to allow insertion of the needle shield (50) into the passageway (117) but prevents the needle shield (50) from exiting through the cut-out when the syringe is removed from the needle shield (50) out of the rear opening of the passageway (117). Preferably, the cut out in the passageway (117) is provided with a raised area that forms a ramp (130). The raised area facilitated entry of the needle shield (50) into the passageway (117). Additionally, the raised area may help to reinforce the inner sidewall (123) of the passageway (117).

The needle shield remover (400) of FIG. 4 is illustrated with rear resilient legs and projections as described with reference to FIGS. 1a-1d. Additionally, the needle shield remover is provided with cut outs and forward resilient legs as described with reference to FIGS. 1a-1d. It will be understood, however, that the needle shield remover may be provided with any suitable means to retain the needle shield (50) within the device when it is removed from a syringe, including but not limited to those means discussed with reference to FIGS. 2a-2e and FIG. 3.

The combined removed needle shield and device are retained until disposal of the needle shield is required, whereupon the needle shield is removed from the device. This is achieved in the first and third embodiments by pulling the partially exposed front portion (51) of the needle shield (50) further in a distal direction through and out of the passageway (117, 217). In the second embodiment, a user presses the actuator (203). This causes the arcuate wall of the biasing member to flex thereby releasing the grip of the locking barrier (205) on the needle shield, allowing the shield to be removed from the passageway.

It will be understood that whilst in the present description the needle shield (50) is removed by the user extracting it from the distal end of the needle shield remover (100, 200, 300, 400), the needle shield (50) may be removed by exerting an increased pressure on the needle shield (50) from the proximal end of the needle shield remover. The increased pressure causes the needle shield to exit the distal end of the passageway (117). The pressure may be provided, for example, by a rear cap which fits onto the proximal end of the needle shield remover and is provided with an projection that extends down the passageway placing a force on the removeable needle shield (50). With reference to the embodiment of FIG. 4 the needle shield remover may be provided with a passageway between the outside to the passageway (117). This passageway allows a tool to be inserted through the passageway and exert a force on the needle shield in order that it exits the device through the cut out. The tool may be, for example, a device configured to fit on the outside of the needle shield remover with a projection on its inside wall. The projection being sized to contact and exert pressure on the needle shield when the device is in contact with the outside wall of the needle shield remover.

The embodiments presented herein are illustrative examples presenting combinations of features of the invention. It should be understood that any feature could be combined with any other feature the same as if each and every combination of features were specifically and individually listed.

The invention claimed is:

1. A needle shield remover for removing a needle shield from a syringe, the needle shield remover comprising
    receiving means comprising a passageway to receive at least part of the needle shield, the passageway being defined by a side wall, and the passageway including a cut-out in at least a portion of the side wall such that a needle shield may be inserted into the passageway through the cut-out;
    removing means comprising a first inward projection to detach the needle shield from the syringe whilst it is present in the passageway; and
    retaining means within a portion of the passageway and positioned distally from the first inward projection to temporarily retain the needle shield in the receiving means after removal of the syringe.

2. A needle shield remover according to claim 1, wherein passageway is defined by a wall of the needle shield remover.

3. A needle shield remover according to claim 2 wherein there is provided a gap in the wall of the passageway to allow the at least part of the needle shield to be received.

4. A needle shield remover according to claim 2 wherein the needle shield is introduced to the receiving means through an end of the passageway.

5. A needle shield remover according to claim 1, wherein the removing means further comprises a friction fit area within the receiving means.

6. A needle shield remover according to claim 1, wherein the first inward projection is located on the passageway such that when the needle shield is inserted into the receiving means the inward projection engages a proximal end of the needle shield.

7. A needle shield remover according to claim 1, wherein said removing means further comprise at least two rearwardly extending legs.

8. A needle shield remover according to claim 1, wherein said removing means further comprise at least two rearwardly extending legs, each of the rearwardly extending legs being provided with an inward projection such that when the needle shield is inserted into the receiving means the inward projection engages a proximal end of the needle shield.

9. A needle shield remover according to claim 1, wherein the retaining means comprises a friction fit area within the receiving means.

10. A needle shield remover according to claim 9, wherein the friction fit area comprises an area of elastomer.

11. A needle shield remover according to claim 5, wherein the friction fit area is provided by a first projection located at, or near to, a front opening of the passageway.

12. A needle shield remover according to claim 11, wherein the first projection is situated on a resilient front leg, the resilient front leg being formed within a recess located at, or near to, the front opening of the passageway.

13. A needle shield remover according to claim 12, wherein said resilient front leg is integral with and extends forwardly from a wall of the passageway at a proximal edge of the recess.

14. A needle shield remover according to claim 1, wherein said retaining means further comprises a barrier mechanism, the barrier mechanism including a barrier member defining a passageway, the barrier member being moveable between a protruding position where the passageway and the passageway of the barrier member are not aligned and a recessed position where the passageway and the passageway of the barrier member are aligned.

15. A needle shield remover according to claim 14, wherein the barrier mechanism comprises an arm, and a resilient biasing member at one end of the arm, the resilient biasing member being configured to contact a wall of the needle shield remover and bias the arm to the protruding position.

16. A needle shield remover according to claim 14 wherein the barrier member is provided with one or more teeth such that the teeth engage with the needle shield when the barrier member is in the protruding position and do not engage with the needle shield when the barrier member is in the recessed position.

17. A needle shield remover according to claim 1 wherein at least a part of the side wall forming an edge of the cut-out forms a ramp thereby facilitating entry of the needle shield into the passageway.

* * * * *